US006316555B1

(12) United States Patent
Schrock et al.

(10) Patent No.: US 6,316,555 B1
(45) Date of Patent: Nov. 13, 2001

(54) LIVING OLEFIN POLYMERIZATION PROCESSES

(75) Inventors: Richard R. Schrock, Winchester; Robert Baumann, Cambridge, both of MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/307,241

(22) Filed: Mar. 4, 1999

Related U.S. Application Data

(63) Continuation of application No. 08/843,161, filed on Apr. 11, 1997, now Pat. No. 5,889,128.

(51) Int. Cl.$^7$ .................................. C08F 4/18; C08F 2/46
(52) U.S. Cl. ........................ 526/107; 526/65; 526/66; 526/72; 526/73; 526/75; 526/78; 526/90; 526/108; 526/126; 526/217; 526/903; 522/63; 522/65; 522/66; 522/68; 522/113; 522/184; 502/150; 502/167; 502/232
(58) Field of Search .................................. 526/65, 66, 72, 526/73, 75, 78, 90, 107, 108, 126, 217, 903; 522/63, 65, 66, 68, 113, 184; 502/150, 167, 232

(56) References Cited

U.S. PATENT DOCUMENTS

| | | |
|---|---|---|
| 4,480,075 | 10/1984 | Willis . |
| 4,681,956 | 7/1987 | Schrock . |
| 4,752,597 | 6/1988 | Turner . |
| 4,791,180 | 12/1988 | Turner . |
| 4,882,406 | 11/1989 | Cozewith et al. . |
| 4,959,436 | 9/1990 | Cozewith et al. . |
| 5,026,798 | 6/1991 | Canich . |
| 5,079,205 | 1/1992 | Canich . |
| 5,196,491 | 3/1993 | Cho et al. . |
| 5,281,368 | 1/1994 | Dias et al. . |
| 5,318,935 | 6/1994 | Canich et al. . |
| 5,391,629 | 2/1995 | Turner et al. . |
| 5,399,626 | 3/1995 | Erickson et al. . |
| 5,422,409 | 6/1995 | Brekner et al. . |
| 5,427,991 | 6/1995 | Turner . |
| 5,438,102 | 8/1995 | Brandes et al. . |
| 5,444,145 | 8/1995 | Brant et al. . |
| 5,475,075 | 12/1995 | Brant et al. . |
| 5,476,915 | 12/1995 | Shea et al. . |
| 5,489,651 | 2/1996 | Novak et al. . |
| 5,502,124 | 3/1996 | Crowther et al. . |
| 5,504,049 | 4/1996 | Crowther et al. . |

(List continued on next page.)

FOREIGN PATENT DOCUMENTS

| | | |
|---|---|---|
| 0 893 454 A1 | 1/1999 | (EP) . |
| WO 91/12285 | 8/1991 | (WO) . |
| WO 92/12162 | 7/1992 | (WO) . |
| WO 94/21700 | 9/1994 | (WO) . |
| WO 97/42197 | 11/1997 | (WO) . |
| WO 98/46651 | 10/1998 | (WO) . |

OTHER PUBLICATIONS

Guerin et al., "Conformationally Rigid Diamide Complexes: Synthesis and Structure of Titanium(IV) Alkyl Derivatives", Organometallics vol. 15, No. 24, pp. 5085–5089, 1996.

Scollard et al., "Living Polymerization of α–Olefins by Chelating Diamide Complexes of Titanium", J.Am.Chem.Soc., vol. 118, No. 41, pp. 10008–10009, 1996.

R. Baumann et al., "Synthesis of Titanium and Zirconium Complexes That Contain the Tridentate Diamido Ligand, $[((t-Bu-d_6)N-o-C_6H_4)_2O]^{2-}([NON]^{2-})$ and the Living Polymerization of 1–Hexene by Activated $[NON]ZrMe_2$", J.Am. Chem. Soc., vol. 119, No. 16, pp. 3830–3831, 1997.

Cloke et al., "Zirconium Complexes incorporating the New Tridentate Diamide Ligand $[(Me_3Si)N\{CH_2CH_2N(SiMe_3)\}_2]^{2-}(L)$; the Crystal Structures of $[Zr(BH_4)_2L]$ and $[ZrCl\{CH(SiMe_3)_2\}L]$", J. Chem. Soc. Dalton Trans., pp. 25–30, 1995.

Clark et al., "Titanium(IV) complexes incorporating the aminodiamide ligand $[(SiMe_3)N\{CH_2CH_2N(SiMe_3) 2\}]^{2-}(L)$; the X–ray crystal structures of $[TiMe_2(L)]$ and $[TiCl\{CH(SiMe_3)2\}(L)]$", Journal of Organometallic Chemistry, vol. 501, pp. 333–340, 1995.

Horton et al., "Cationic Alkylzirconium Complexes Based on a Tridentate Diamide Ligand: New Alkene Polymerization Catalysts", Organometallics, vol. 15, No. 12, pp. 2672–2674, 1996.

Yasuo, "Production of Alkenecarboxylic Acid Ester", Patent Abstracts of Japan, Pub. No. 08081415, Pub. Date Mar. 26, 1996.

Di Silvestro et al., "Polymerization of propene with enantiomorphic site catalysts, 1 A statistical analysis", Macromol. Chem. Phys. vol. 197, pp. 3209–3228, 1996.

Støvneng & Rytter, "Influence of rotation between agostic structures on ethene interaction with a zirconocene polymerization site", Journal of Organometallic Chemistry, vol. 519, pp. 205–208, 278, 1996.

Primary Examiner—Samuel A. Acquah
(74) Attorney, Agent, or Firm—Wolf, Greenfield & Sacks, P.C.

(57) ABSTRACT

Processes for the living polymerization of olefin monomers with terminal carbon-carbon double bonds are disclosed. The processes employ initiators that include a metal atom and a ligand having two group 15 atoms and a group 16 atom or three group 15 atoms. The ligand is bonded to the metal atom through two anionic or covalent bonds and a dative bond. The initiators are particularly stable under reaction conditions in the absence of olefin monomer. The processes provide polymers having low polydispersities, especially block copolymers having low polydispersities. It is an additional advantage of these processes that, during block copolymer synthesis, a relatively small amount of homopolymer is formed.

26 Claims, No Drawings

U.S. PATENT DOCUMENTS

| | | |
|---|---|---|
| 5,599,761 | 2/1997 | Turner . |
| 5,602,219 | 2/1997 | Aulbach et al. . |
| 5,610,253 | 3/1997 | Hatke et al. . |
| 5,612,428 | 3/1997 | Winter et al. . |
| 5,621,126 | 4/1997 | Canich et al. . |
| 5,635,573 | 6/1997 | Harrington et al. . |
| 5,693,730 | 12/1997 | Kuber et al. . |
| 5,698,645 | 12/1997 | Weller et al. . |
| 5,723,560 | 3/1998 | Canich . |
| 5,741,868 | 4/1998 | Winter et al. . |
| 5,763,556 | 6/1998 | Shaffer et al. . |
| 5,789,474 | 8/1998 | Lu et al. . |
| 5,840,808 | 11/1998 | Sugimura et al. . |

LIVING OLEFIN POLYMERIZATION PROCESSES

This application is a continuation of Ser. No. 08/843,161 filed Apr. 11, 1997 U.S. Pat. No. 5,889,128.

BACKGROUND OF THE INVENTION

1. Field of the Invention

The present invention relates generally to living olefin polymerization processes, and more specifically to initiators for such processes that are stable under reaction conditions in the absence of olefin monomer such that polymers of low polydispersity can be synthesized.

2. Discussion of the Related Art

Polymers are used in a large number of applications, and a great deal of attention has been paid to developing synthetic routes that result in polymers having optimal physical and chemical properties for a given application.

Block copolymers are one class of polymers that have broad utility. For example, block copolymers have been employed as melt processable rubbers, impact resistant thermoplastics and emulsifiers. As a result, these materials have been the focus of a particularly large amount of research and development both in industry and academia, and a variety of approaches to block copolymer synthesis have been developed.

When preparing a block copolymer, it is generally desirable to use a synthetic technique that allows for control over the chain length of each polymer block and the polydispersity of the resulting block copolymer. For some time, attempts to provide such a method have focused on block copolymer formation by living polymer synthesis. In living polymer synthesis, a metal-containing initiator having either a metal-carbon bond or a metal-hydrogen bond is reacted with an olefin monomer to form a polymer chain via the successive insertion of the first olefin monomer into a metal-carbon bond between the metal of the initiator and the growing polymer chain. If the initiator is a metal-hydride complex, the first metal-carbon bond is formed when the olefin inserts into the metal-hydride bond. When the olefin monomer is depleted, a second olefin monomer is added, and a second polymer block is formed by successively inserting, into the metal-carbon end group, the second monomer, ultimately resulting in a block copolymer including a first polymer block connected to a second polymer block. Since each polymer block is formed sequentially, the initiator and propagating species should be stable under reaction conditions in the absence of olefin monomer.

To provide a block copolymer having sizable polymer blocks of low polydispersity, the rate of chain propagation (i.e., olefin monomer insertion into the metal-carbon bond) should be substantially greater than the rate of chain termination or transfer. To prepare a block copolymer having the lowest possible polydispersity, the rate of initiation should be at least as great as the rate of propagation.

Polymerization termination is typically dominated by β-hydride elimination with the products being a polymer chain having a terminal carbon-carbon double bond and the initiator having a metal-hydrogen bond. Termination of polymerization also can occur if the initiator decomposes in some other manner, such as transfer of the polymer chain from the initiator to some other element that is relatively inactive in or for olefin polymerization. Hence, the achievable chain length of copolymer blocks and the polydispersity of the block copolymer are principally determined by the relative rates of olefin insertion and β-hydride elimination, as well as initiator stability toward other modes of decomposition, especially in the absence of olefin monomer.

Attempts at synthesizing polymers using living polymer synthesis have employed a variety of initiators. For example, as reported in *JACS* 118, 10008 (1996), McConville and co-workers have used a diamido-titanium initiator to form polymers by polymerizing α-olefins. In addition, Turner and co-workers have developed a hafnium-containing cyclopentadienyl initiator for preparing block copolymers from α-olefin monomers (published PCT patent application WO 91/12285). Furthermore, Horton and co-workers report diamido-group IVB metal initiator effective in providing homopolymer synthesis (*Organometallics* 15, 2672 (1996)).

Despite the commercial motivation for developing a living polymer synthetic method for block copolymer preparation, known methods of block copolymer synthesis can suffer from a variety of problems. For example, the initiators used can be unstable under reaction conditions in the absence of olefin monomer, resulting in an inability to form additional homopolymer blocks to form a block copolymer. Moreover, the efficiency of block copolymer formation can be reduced due to the formation of significant amounts of homopolymer. In addition, due to the low temperatures used, the products formed using many known initiators have relatively low molecular weights and are more appropriately classified as oligomers.

As seen from the foregoing discussion, it remains a challenge in the art to provide a method of synthesizing block copolymers that includes the use of a initiator that is stable in the absence of olefin monomer such that the resulting block copolymers have low polydispersities. Such an initiator would also offer the advantage of resulting in relatively small amounts of homopolymer synthesis.

SUMMARY OF THE INVENTION

In one illustrative embodiment, the present invention provides a composition of matter having a structure:

$$[R_1{-}X{-}A{-}Z{-}R_2]^{2-}$$

X and Z are each group 15 atoms. $R_1$ and $R_2$ are each a hydrogen atom or group 14 atom-containing species. A is either

or

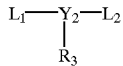

$Y_1$ is a group 16 atom, and $Y_2$ is a group 15 atom. $R_3$ is H or a group 14 atom-containing species. $L_1$ and $L_2$ are each dative interconnections including at least one group 14 atom bonded to $Y_1$ or $Y_2$.

In another illustrative embodiment, the present invention provides a method of synthesizing a block copolymer. The method comprises performing a first reaction and a second reaction. In the first reaction, a first monomeric species containing a terminal carbon-carbon double bond is exposed to an initiator containing a metal, and the terminal carbon-carbon double bonds of the first monomeric species are allowed to insert successively into the initiator to form a carbon-metal bond thereby forming a first homopolymeric block of the first monomeric species connected to the metal of the initiator. In the second reaction, a second monomeric species containing a terminal carbon-carbon double bond is exposed to the initiator, and terminal carbon-carbon double bonds of the second monomeric species are allowed to insert successively into the initiator, first inserting into the bond between the block of the first homopolymeric block and the metal of the initiator, thereby forming a copolymer including the first homopolymeric block connected to a homopolymeric block of the second monomeric species, the copolymer having a polydispersity of no more than about 1.4.

In yet another illustrative embodiment, the present invention provides a method of synthesizing a block copolymer. The method comprises: exposing a first monomeric species having a terminal carbon-carbon double bond to an initiator including a metal and allowing terminal carbon-carbon double bonds of the first species to insert successively into the initiator to form a metal-carbon bond thereby forming a first homopolymeric block of the first monomeric species having a bond to the metal of the initiator; and exposing a second monomeric species containing a terminal carbon-carbon double bond to the initiator and allowing terminal carbon-carbon double bonds of the second species to insert successively into the initiator, first inserting into the bond between the first homopolymeric block and the metal, thereby forming a copolymer including the first homopolymeric block connected to a second homopolymeric block of the second monomeric species, the method producing no more than about 25% by weight of the first homopolymer or the second homopolymer relative to a total amount of polymer product.

In a further illustrative embodiment, the present invention provides a block copolymer which comprises a first homopolymer block and a second homopolymer block connected to the first homopolymer block. The first homopolymer block comprises a polymerization product of at least about ten units of a first monomeric species having a formula $H_2C=CHR_1$. The second homopolymer block comprises a polymerization product of at least about ten units of a second, different monomeric species having a formula $H_2C=CHR_2$. $R_1$ and $R_2$ can be the same or different, and each are H or a linear, branched, or cyclic hydrocarbon that is free of non-carbon heteroatoms. The block copolymer has a polydispersity of at most about 1.4.

In still a further illustrative embodiment, the present invention provides a method of polymerization. The method comprises: reacting an initiator having a metal atom with a monomeric species having a terminal carbon-carbon double bond to allow terminal carbon-carbon double bonds of monomers to insert successively into the initiator to form a metal-capped polymer of the monomeric species connected to the metal through a metal-carbon bond. The metal-capped polymer is stable, in a solvent essentially free of the monomeric species and electron donors such as water and free oxygen at a temperature of at least about −50° C. The metal-capped polymer is capable of then reacting further with monomeric species and inserting the monomeric species successively into a metal carbon bond.

DETAILED DESCRIPTION

In one aspect, the present invention relates to a ligand (referred to herein as [LIG]) having the following representative structures:

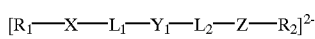

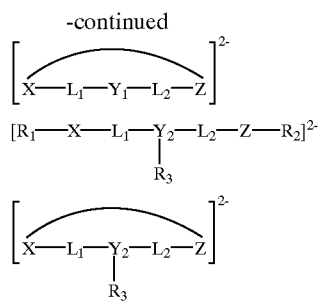

X and Z are group 15 atoms such as nitrogen and phosphorous that are each selected to form an anionic or covalent bond with a metal atom, particularly a transition metal, while simultaneously including two substituents (e.g., $L_1$ and $R_1$ or $L_2$ and $R_2$). $Y_1$ is a group 16 atom such as oxygen or sulfur that is selected to form a dative bond with another atom such as a metal atom, particularly a transition metal, while simultaneously including two substituents (e.g., $L_1$ and $L_2$). $Y_2$ is a group 15 atom such as nitrogen or phosphorus that is selected to form a dative bond with another atom such as a metal atom, particularly a transition metal, while simultaneously including three substituents (e.g., $L_1$, $L_2$ and $R_3$). ⌢ represents a dative interconnection between X and Z, such as one or more group 14 atoms. In certain embodiments, $Y_1$ is preferably oxygen and X and Z are the same atom, more preferably, X and Z are each nitrogen atoms.

A "dative bond" herein refers to a bond between a neutral atom of a ligand and a metal atom in which the neutral atom of the ligand donates an electron pair to the metal atom. As used herein, an "anionic bond" denotes a bond between a negatively charged atom of a liaand and a metal atom in which the negatively charged atom of the ligand donates an electron pair to the metal atom.

$L_1$ and $L_2$ each represent a dative interconnection between X, $Y_1$, $Y_2$ and/or Z. $L_1$ and $L_2$ each correspond to at least one atom, preferably 1–4 atoms, and most preferably 2 atoms. The atoms that make up the interconnection most commonly are group 14 atoms, such as carbon or silicon. Preferably, $L_1$ and $L_2$ each represent a $C_2$ unit such as —$(CH_2)_2$—, —$(CF_2)_2$—, —(o-$C_6H_4$)—, —$CH_2Si(CH_3)_2$— and the like. In certain embodiments, $L_1$ and $L_2$ may be selected such that X, $Y_1$, $Y_2$ and/or Z are not rigidly interconnected (i.e., there is at least one rotational degree of freedom between these atoms).

Although depicted in an arrangement in which X is interconnected to $Y_1$ or $Y_2$ and $Y_1$ or $Y_2$ is interconnected to Z, other arrangements of X, $Y_1$ or $Y_2$ and Z are envisioned to be within the scope of the present invention. For example, in certain embodiments, X may be interconnected to Z through $L_1$ or $L_2$. The arrangement of X, $Y_1$ or $Y_2$ and Z is limited only in that, simultaneously, X and Z should each be selected to form anionic or covalent bonds with a metal atom such as a transition metal while $Y_1$ or $Y_2$ should each be selected to form a dative bond with a metal atom such as a transition metal. Upon reading this disclosure, those of ordinary skill in the art will recognize a combination of atoms X, $Y_1$, $Y_2$ and Z, and interconnections $L_1$ and $L_2$ that will provide this capability.

$R_1$–$R_3$ can be the same or different and preferably are H or group 14 species such as linear, branched, cyclic and/or aromatic hydrocarbons free of non-group 14 heteroatoms that could bind to an activated metal center. One set of exemplary $R_1$–$R_3$ units include saturated or unsaturated straight, branched or cyclic hydrocarbons. Another example of $R_1$–$R_3$ units is trimethylsilyl groups. Still a further example of $R_1$–$R_3$ units is 2,6-disubstituted phenyl rings such as 2,6-dimethylphenyl.

In another aspect, the invention relates to metal-containing catalyst precursors, preferably group 4 metal-containing catalyst precursors, for use in the living polymerization of olefin monomers having terminal carbon-carbon double bonds. These catalyst precursors are particularly stable under reaction conditions in the absence of such olefin monomer. That is, when the reaction mixture is substantially depleted of the olefin monomer, the catalyst precursor remains stable in the absence of water, oxygen, basic donor ligands and the like. As a result of the catalyst precursor's stability, the resulting polymers (e.g., homopolymers, random copolymers and/or block copolymers) have low polydispersities. Furthermore, when used to prepare block copolymers, the amount of homopolymer produced is relatively low.

Substantial depletion of an olefin monomer relates to a situation in which the olefin monomer is present in an amount below the detection limit of standard NMR spectrometers such that the olefin monomer cannot be detected using such standard NMR spectrometers. Typically, an olefin monomer is substantially depleted when less than about 5% of the olefin monomer remains as olefin monomer in solution relative to the amount of olefin monomer initially present in the solution.

The catalyst precursors of the present invention have the following representative molecular structures:

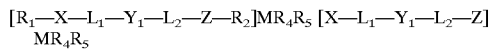

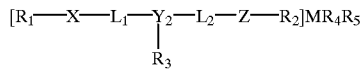

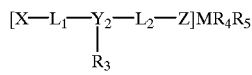

That is,:

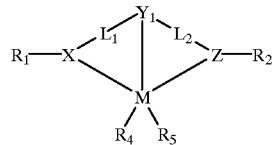

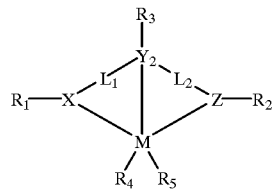

M is a metal atom that can form a metal-carbon bond into which an olefin can be inserted. Those of ordinary skill in the art will recognize metals that meet this requirement. For example, M may be selected from metals of groups 3–6, late transition metals such as those of group 10, actinides and lanthanides. In one set of preferred embodiments, M is selected from Ti, Zr or Hf. X and Z each form an anionic or covalent bond to M while $Y_1$ or $Y_2$ each form dative bonds to M. Preferably, the length of the M—$Y_1$ and M—$Y_2$ bonds is at most about 2.5 Angstroms, more preferably at most about 2.3 Angstroms, most preferably at most about 2.1 Angstroms, depending upon the size of M.

$R_4$ and $R_5$ should be good leaving groups such that living polymerization can occur via the removal of $R_4$ or $R_5$ and the formation of an initiator, as described below. Typically, $R_4$ and $R_5$ are substantially similar to $R_1$–$R_3$. Preferably, $R_4$ and $R_5$ are linear or branched alkyls having a length of from 1–10 carbon atoms. In some embodiments $R_4$ and/or $R_5$ can be hydrogen.

The present invention is not limited by the particular geometrical configuration of the catalyst precursor. However, in certain embodiments, the catalyst precursor may have a nonplanar geometry, such as, for example, trigonal bipyramidal. In some embodiments, it is preferable that the catalyst precursor have a geometrical configuration such that X, $Y_1$ or $Y_2$ and Z are interconnected in the same plane.

In a particularly preferred set of embodiments, a catalyst precursor is provided having one of the structures:

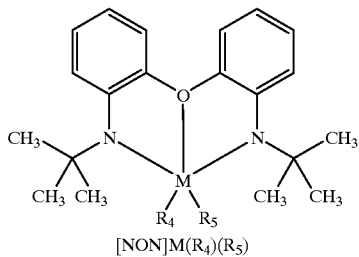

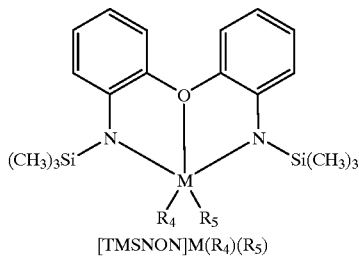

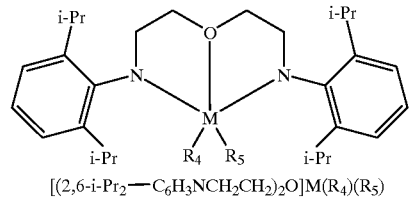

It is to be noted that, in certain embodiments, any or all of the isopropyl groups of [(2,6-i—$Pr_2$—$C_6H_3NCH_2CH_2)_2O$]M($R_4$)($R_5$) may be replaced with H or branched or straight chain alkyl groups. As will be appreciated by one skilled in the art, such alkyl groups should be selected such that an olefin monomer's access to M during polymerization (described below) is not sterically hindered by these alkyl groups. Typically, such alkyl groups have at most about 20 carbon atoms and include, for example, methyl, propyl, t-butyl and the like.

The catalyst precursors can be prepared using standard alkylation techniques. For example, the protanated ligand ($H_2$[LIG]) can be reacted with M($NMe_2$)$_4$ to form [LIG]M($NMe_2$)$_2$ which is then reacted with TMSCl to form [LIG]MCl$_2$. The [LIG]MCl$_2$ is reacted with R-MgX to provide [LIG]MR$_2$. The appropriate reaction conditions of from about −78° C. to about 0° C. in a solvent such as ether, diethyl ether, hydrocarbons, free of oxygen and water, can be selected by those of skill in the art. Alternatively, [LIG]MCl$_2$ can be reacted with aluminoxane which first reacts to form the dimethyl compound [LIG]M(Me)$_2$ in situ, and then removes one Me group to make the active cation, serving as its counterion. This reaction is known, as described in, for example, published PCT patent application WO 92/12162.

During living polymerization, the catalyst precursor is activated via the removal either R$_4$ or R$_5$, typically in situ, to form an initiator which is cationic in nature. Where a stable salt can be synthesized, this salt can be provided, stored, and used directly. Counterions for the initiator should be weakly-coordinating anions, for example [B(C$_6$F$_5$)$_4$]$^-$. Those of ordinary skill in the art can select suitable counter ions.

The initiator can be reacted with monomeric olefins having a terminal carbon-carbon double bond (H$_2$C=CHR$_6$) to provide polymers, where R$_6$ is hydrogen or a hydrocarbon such that the olefin can be a straight, branched, cyclic or aromatic hydrocarbon. Furthermore, the hydrocarbons may include additional carbon-carbon double bonds. Preferably, any additional carbon-carbon double bonds are internal (non-terminal). Preferably, these monomers are substantially devoid of any heteroatoms. Examples of such monomers include, but are not limited to, α-olefins such as ethylene, 1-propylene, 1-butene, 1-hexene, 1-heptene, 1-octene, 1-nonene, 1-decene, 4-methyl-1-pentene and the like.

Initiation of the polymerization reaction occurs by insertion of the carbon-carbon double bond of the species H$_2$C=CHR$_6$ into a metal-carbon bond of the initiator. During reaction of the initiator and monomeric olefin, chain growth of the polymer occurs by successive insertion of the monomer into a bond formed between the terminal carbon atom of the polymer chain and the metal atom of the initiator. It is an advantageous feature of the present invention that, under reaction conditions in the absence of monomer (described above), such a metal-carbon bond remains stable for periods of time sufficient to allow depletion of monomer and subsequent addition of monomer and continued chain growth. For example, the system allows depletion of one monomer H$_2$C=CHR$_6$, and addition to the system of a additional monomer H$_2$C=CHR$_7$ that can be the same monomer (for continued homopolymer growth) or a different monomer (for block copolymer synthesis). Preferably, a metal-carbon bond of the initiator, such as a bond between the metal and a polymer chain, remains stable for greater than about a half an hour at room temperature under reaction conditions in the absence of olefin monomer, water, oxygen, basic donor ligands or the like. For most known initiators used in polymerizing these monomers, the metal-carbon bond formed between the initiator and the polymer chain is not stable enough for standard analytical techniques, such as NMR, to verify the existence of the initiator, indicating that the initiator-polymer chain species is not stable for more than at most about one second at room temperature. In contrast, the initiating and propagating species of the present invention have been verified by NMR.

This enhanced stability of this metal-carbon bond is desirable because blocks of polymer may be formed in a sequential fashion by adding olefin monomer, allowing the olefin monomer to react until it is depleted and subsequently adding more olefin monomer. When forming block copolymers, a first block of the copolymer may be formed (first homopolymeric block). Upon depletion of the first monomeric olefin, the carbon-metal bond remains stable and a second olefin monomer may be added to the reaction mixture to form a second homopolymeric block that is connected to the first homopolymeric block. During this reaction, the second olefin monomer first inserts into the metal-carbon bond formed between the first homopolymeric block and the initiator. Subsequently, the second olefin monomer successively inserts into the metal-carbon bond formed between the initiator and the polymer chain of the second olefin monomer.

As a result of the initiator's stability, polymers are formed with relatively low polydispersities. The "polydispersity" of a polymer as used herein refers to the ratio of the weight average molecular weight (Mw) to the number average molecular weight (Mn) of the polymer according to equation 1.

$$\text{POLYDISPERSITY} = \frac{\sum_i N_i M_i^2}{\sum_i N_i M_i} \quad (1)$$

where $N_i$ is the number of mer units having molecular weight $M_i$.

In particular, the present invention can provide block copolymers having low polydispersities. Known block copolymers have been synthesized using anionic polymerization processes, but α-olefin monomers cannot be used in these processes. In known block copolymers, typical minimal polydispersities are on the order of about 1.5. According to the present invention, block copolymers preferably have a polydispersity of at most about 1.4, more preferably from about 1 to about 1.3, more preferably from about 1 to about 1.2, more preferably from about 1 to about 1.1, and most preferably from about 1 to 1.05. The polydispersity of a polymer can be measured directly by a variety of techniques including, for example, gel permeation chromatography or by standard tests such as the ASTM D-1238 procedure.

It is a further advantage of the present invention that the initiator's stability results in good block copolymer formation with minimal formation of polymers formed substantially only of individual monomeric olefin units (homopolymer). That is, relatively highly pure block copolymer is formed. In known systems, the amount of homopolymer formed is typically about 30 wt % based on the total amount of polymer formed including the block copolymer. According to the present invention, the amount of homopolymer formed is at most about 25 wt % based on the total amount of polymer formed including copolymer, more preferably at most about 15 wt %, and most preferably at most about 5 wt %. These purity levels are preferably realized in combination with preferred polydispersity levels discussed above. For example, one embodiment involves formation of block copolymer of polydispersity of less than about 1.4 with homopolymer formation of at most about 25 wt % based on the total amount of polymer formed including copolymer.

Most known block copolymer synthesis methods are conducted at temperatures of at most about −78° C. At these low temperatures, it is difficult to form polymers. Instead, oligomers having less than 50 mer units typically are formed. It is a further advantage of the present invention that living polymerization processes can be successfully conducted at relatively high temperatures. Preferably, living polymerization occurs at a temperature of at least about −50° C., more preferably at least about 0° C., most preferably at least about 25° C. At these higher temperatures in connection with the present invention, polymer blocks having at least about 50 mer units, preferably at least about 75 mer units, and most preferably at least about 100 mer units can be formed.

The initiators of the present invention can be used for polymerization of a variety of combinations of monomers to form homopolymers, random copolymers of any number or ratio of monomers, or block copolymers of any number and size of blocks, while providing optionally the preferred polydispersities and/or purities discussed above. For example, two monomers A and B ($H_2C$=$CHR_6$ and $H_2C$=$CHR_7$) in a ratio of 2:1 can first be provided in a reaction system, with polymerization resulting in a random copolymer with A and B being incorporated in a ratio of 2:1, after depletion of these monomers. Then, because of the stability of the initiator, additional monomers C and D can be added to the system, and further polymerization will result in a product having a first block of random AB and a second block of random CD. As discussed, blocks of relatively pure homopolymer can be provided. For example, polymerization of A until depletion of A, followed by addition of B and polymerization of B resulting in a block copolymer AB.

The following examples indicate certain embodiments of the present invention. These examples are illustrative only and should not be construed as limiting.

All air sensitive manipulations were conducted under a nitrogen atmosphere in a Vacuum Atmospheres drybox or under argon when using Schlenk techniques. Pentane was washed with sulfuric/nitric acid (95/5 v/v), sodium bicarbonate, and then water, stored over calcium chloride, and then distilled from sodium benzophenone ketyl under $N_2$. Reagent grade diethyl ether, 1,2-dimethoxyethane, 1,4-dioxane, and tetrahydrofuran were distilled from sodium. Deuterated solvents were passed through activated alumina and vacuum transferred to solvent storage flasks until use. Proton and carbon spectra were referenced using the partially deuterated solvent as an internal reference. Fluorine spectra were referenced externally. Chemical shifts are reported in ppm and coupling constants are in hertz. All spectra were acquired at about 22° C. unless otherwise noted. IR spectra were recorded on a Perkin-Elmer FT-IR 16 spectrometer as Nujol mulls between KBr plates in an airtight cell. Microanalyses (C, H, N) were performed on a Perkin-Elmer PE2400 microanalyzer in our laboratory. Since the elemental analyzer measures moles of water, the %H was calculated assuming all D present was H, but the actual molecular mass was employed. GPC analyses were carried out on a system equipped with two Alltech columns (Jordi-Gell DVB mixed bed –250 mm×10 mm (i.d.)). The solvent was supplied at a flow rate of 1.0 mL/min. with a Knauer HPLC pump 64. HPLC grade $CH_2Cl_2$ was continuously dried and distilled from $CaH_2$. A Wyatt Technology mini Dawn light scattering detector coupled to a Knauer differential-refractometer was employed. The differential refractive index increment, dn/dc, was determined assuming that all polymer that was weighed for the run (usually about 5 mg to ±0.1 mg) eluted from the column. For poly(1-hexene) polymers, to minimize polymer weighing error the average value for dn/dc (0.049 mL/g) from 18 runs (0.045 to 0.053 mL/g) was employed and the molecular weights recalculated. The yields for poly(1-hexene) were essentially quantitative (about 97% to about 100%).

EXAMPLE 1

[NON]Ti(NMe$_2$)$_2$ was synthesized as follows. LiBu (1.6 M in hexane, 4.2 mL) was added to a solution of H$_2$[NON] (1.09 g, 3.36 mmol) in diethyl ether (30 mL) at –35° C. The mixture was warmed to room temperature and stirred for 4 h. A suspension of TiCl$_2$(NMe$_2$)$_2$ (696 mg, 3.36 mmol) in diethyl ether (20 mL) was added to the solution containing the Li$_2$[NON] at –35° C. The mixture was warmed to room temperature and stirred for 15 h. After filtration through Celite all volatiles were removed in vacuo. The residue was dissolved in a minimum of methylene chloride and layered with pentane. Cooling to –35° C. afforded orange crystalline solid; yield 864 mg (56%): $^1$H NMR (C$_6$D$_6$) δ 6.92 (m, 6H), 6.63 (m, 2H), 3.13 (s, 12H, NMe$_2$), 1.28 (s, 6H, CMe(CD$_3$)$_2$); $^{13}$C NMR δ (C$_6$D$_6$) 150.93, 147.12, 124.37, 123.28, 120.29, 118.60, 60.20, 47.84, 32.43, 31.93(m).

EXAMPLE 2

[NON]TiCl$_2$ was synthesized as follows. A Schlenk tube was charged with [NON]Ti(NMe$_2$)$_2$ (379 mg, 0.83 mmol), TMSCl (270 mg, 2.49 mmol) and toluene (10 mL). The solution was heated to 110° C. for 7 days, during which time the color of the solution turned black-purple. The volatile components were removed in vacuo and the residue recrystallized from methylene chloride/pentane at –35° C.; yield 286 mg (78%): $^1$H NMR (C$_6$D$_6$) δ 6.84 (m, 4H), 6.57 (m, 4H), 1.33 (s, 6H, CMe(CD$_3$)$_2$); $^{13}$C NMR (C$_6$D$_6$) δ 147.78, 142.14, 126.71, 124.41, 120.58, 118.86, 64.77, 30.57, 30.35 (m). Anal. Calcd for C$_{20}$H$_{14}$D$_{12}$Cl$_2$N$_2$OTi: C, 54.43; H, 5.89; N, 6.35. Found: C, 54.57; H, 5.96; N, 6.13.

EXAMPLE 3

[NON]TiMe$_2$ was synthesized as follows. A solution of MeMgCl in THF (3.0 M, 350 μL) was added to a solution of [NON]TiCl$_2$ (230 mg, 0.52 mmol) in ether (10 mL) at –35° C. The color immediately changed from dark purple to orange and white solid precipitated. The mixture was warmed to room temperature and stirred for 15 min. All volatiles were removed in vacuo and the residue extracted with pentane (about 10 mL) over a period of about 5 min. The mixture was filtered through Celite and the pentane removed in vacuo to afford an orange red solid which was recrystallized from a mixture of ether and pentane at –35° C.; yield 162 mg (78%): $^1$H NMR δ 6.87 (m, 6H), 6.56 (m, 2H), 1.60 (s, 6H, TiMe$_2$,) 1.42 (s, 6H, CMe(CD$_3$)$_2$); $^{13}$C NMR (C$_6$D$_6$) δ 148.49, 143.47, 126.1, 122.05, 121.42, 119.31, 64.58, 60.15, 31.37, 30.85 (m). Anal. Calcd for C$_{22}$H$_{20}$D$_{12}$N$_2$OTi: C, 65.98; H, 8.05; N, 6.99. Found: C, 66.07; H, 7.94; N, 6.84.

EXAMPLE 4

[NON]Zr(NMe$_2$)$_2$ was synthesized as follows. H$_2$[NON] (6.48 g, 20 mmol) and Zr(NMe$_2$)$_4$ (5.34 g, 20 mmol) were dissolved in pentane (40 mL). Upon standing at room temperature colorless crystals precipitated. After 2 days the solid was filtered off (6.9 g). The supernatant was concentrated and cooled to –35° C. overnight yielding a second crop of colorless solid (1.15 g); total yield 8.05 g (80%): $^1$H NMR (C$_6$D$_6$) δ 6.97 (m, 6H), 6.55 (m, 2H), 2.94 (s, 12H, NMe$_2$), 1.33 (s, 6H, CMe(CD$_3$)$_2$); $^{13}$C NMR (C$_6$D$_6$) δ 147.79, 145.67, 125.62, 122.39, 118.25, 117.84, 57.04, 43.60, 32.06, 31.99 (m). Anal. Calcd for C$_{24}$H$_{26}$D$_{12}$N$_4$OZr: C, 57.43; H, 7.57; N, 11.16. Found: C, 57.56; H, 7.76; N, 11.16.

EXAMPLE 5

[NON]ZrI$_2$ was synthesized as follows. A Schlenk tube was charged with [NON]Zr(NMe$_2$)$_2$ (3.5 g, 7.0 mmol), methyl iodide (15 g, 106 mmol), and toluene (100 mL). The pale yellow solution was heated to 50° C. for two days, during which time white Me$_4$NI precipitated from the reaction and the color of the solution turned bright orange. The Me$_4$NI was filtered off, the solvents were removed from the filtrate in vacuo, and the residue was washed with pentane (10 mL) to afford a yellow solid. The crude product can be recrystallized from toluene layered with pentane, but was used in subsequent reactions without further purification; yield 4.14 g (89%): $^1$H NMR (C$_6$D$_6$) δ 6.79 (m, 6H), 6.56 (m, 2H), 1.36 (br s, 6H, CMe(CD$_3$)$_2$); $^{13}$C NMR (C$_6$D$_6$, 70° C.) δ 146.83, 139.43, 127.90, 123.95, 123.29, 119.42, 60.21, 31.26, 30.71 (m). Anal. Calcd for C$_{20}$H$_{14}$D$_{12}$I$_2$N$_2$OZr: C, 35.98; H, 3.93; N, 4.20. Found: C, 35.71; H, 3.94; N, 3.88.

EXAMPLE 6

[NON]ZrMe$_2$ was synthesized as follows. A solution of MeMgI in diethyl ether (2.8 M, 2.3 mL) was added to a suspension of [NON]ZrI$_2$ (2.119 mg, 3.17 mmol) in diethyl ether (50 mL) at −35° C. The reaction mixture was allowed to warm to room temperature and was stirred until the yellow solid was replaced by white precipitate (30 min). All volatile solvents were then removed in vacuo and the off-white residue was extracted with pentane (50 mL). The extract was filtered and the pentane was removed in vacuo. The crude product was recrystallized from a mixture of pentane and ether to afford pale yellow crystals; yield 1.02 g (72%): $^1$H NMR (C$_6$D$_6$) δ 6.90 (m, 6H), 6.53 (m, 2H), 1.36 (s, 6H, CMe(CD$_3$)$_2$), 0.84 (s, 6H, ZrMe$_2$); $^{13}$C NMR (C$_6$D$_6$) δ 148.08, 142.87, 126.50, 122.46, 120.13, 119.28, 57.00, 45.60, 31.13, 30.59 (m). Anal. Calcd for C$_{22}$H$_{20}$D$_{12}$N$_2$OZr: C, 59.54; H, 7.21; N, 6.31. Found: C, 59.81; H, 7.19; N, 6.39.

EXAMPLE 7

{[NON]ZrMe}[MeB(C$_6$F$_5$)$_3$] was synthesized as follows. A solution of B(C$_6$F$_5$)$_3$ (35 mg, 67 μmol) in pentane (5 mL) that had been cooled to −35° C. was added to a solution of [NON]ZrMe$_2$ (30 mg, 67 μmol) in pentane (5 mL). The mixture immediately turned bright yellow. A solid precipitated when the B(C$_6$F$_5$)$_3$ solution was added at −35° C., but it dissolved when the mixture was warmed to room temperature. The slightly cloudy bright yellow solution was stirred at room temperature for 5 min, filtered, and cooled to −35° C. for two days. Yellow crystals were filtered off and briefly dried in vacuo; yield 31 mg (47%): $^1$H NMR (C$_6$D$_5$Br) δ 7.03–6.55 (m, 8H), 2.24 (br s, 3H, BMe), 0.98 (s, 6H, CMe(CD$_3$)$_2$), 0.77 (s, 3H, ZrMe); $^{13}$C NMR (toluene-d$_8$, −30 ûC) δ 150.24, 147.16, 141.5 (m, C$_6$F$_5$), 139.5 (m, C$_6$F$_5$), 137.77, 135.8 (m, C$_6$F$_5$), 123.54, 59.20, 50.90 (s, ZrMe), 29.5 (br m, $^t$Bu, B-Me); $^{19}$F NMR (C$_6$D$_6$) δ −133.14 (d, 6F, F$_o$), −159.35 (br s, 3F, F$_p$), −164.27 (t, 6F, F$_m$).

EXAMPLE 8

{[NON]ZrMe(PhNMe$_2$)]}[B(C$_6$F$_5$)$_4$] was synthesized as follows. Solid [NON]ZrMe$_2$ (~8 mg, 18 μmol) was added to a suspension of [PhNMe$_2$H][B(C$_6$F$_5$)$_4$] (15 mg, 18 μmol) in C$_6$D$_5$Br(1 mL) at −35° C. and the mixture was stirred for 30 min at room temperature. $^1$H NMR (C$_6$D$_5$Br) δ 6.94–6.50 (m, 13H), 2.74 (s, 6H, PhNMe$_2$), 1.17 (s, 6H, C(CD$_3$)$_2$Me), 0.95 (s, 3H, ZrMe); $^{19}$F NMR (C$_6$D$_5$Br) −131.78 (F$_o$), −162.11 (t, F$_p$), −165.94 (br m, F$_m$).

EXAMPLE 9

Ethylene was polymerized using {[NON]ZrMe}[MeB(C$_6$F$_5$)$_3$] as follows. A stock solution of B(C$_6$F$_5$)$_3$ (51 mg, 100 μmol) in toluene (5 mL) was added to [NON]ZrMe$_2$ (44 mg, 100 μmol) dissolved in toluene (5 mL) at −35° C. The color changed to bright yellow. The reaction mixture was allowed to warm to room temperature. Aliquots were used for polymerization reactions. A solution of {[NON]ZrMe}[MeB(C$_6$F$_5$)$_3$] in toluene (2 mL, 20 μmol) was added to toluene (50 mL) and the solution was stirred vigorously under 1 atm of ethylene. White polyethylene began to precipitate. After 120 sec the reaction was stopped by addition of methanol (5 mL). All solvents were removed in vacuo and the polyethylene was washed with methanol and dried; yield 69 mg.

EXAMPLE 10

Ethylene was polymerized using {[NON]ZrMe(PhNMe$_2$)]}[B(C$_6$F$_5$)$_4$] as follows. A stock solution of [NON]ZrMe$_2$ (44 mg, 100 μmol) in chlorobenzene (5 mL) was added to [PhNMe$_2$H][B(C$_6$F$_5$)$_4$] (80 mg, 100 μmol) dissolved in chlorobenzene (5 mL) at −35° C. The solution was allowed to warm to room temperature. Aliquots were employed for polymerization reactions. A solution of {[NON]ZrMe(PhNMe$_2$)]}[B(C$_6$F$_5$)$_4$] in chlorobenzene (2 mL, 20 μmol) was added to chlorobenzene (50 mL) and the mixture was stirred vigorously under 1 atm of ethylene. The reaction mixture became increasingly viscous as white polyethylene formed and precipitated. After two minutes the reaction was stopped by addition of methanol (3 mL). The volume of the mixture was reduced in vacuo and the polyethylene was precipitated by adding a large excess of methanol. The polymer was filtered off and dried in vacuo; yield 540 mg.

EXAMPLE 11

1-Hexene was polymerized using {[NON]ZrMe(PhNMe$_2$)]}[B(C$_6$F$_5$)$_4$] as follows. In a typical experiment varying amounts of hexene (0.3–3.0 mL) were added to a solution of {[NON]ZrMe(PhNMe$_2$)]}[B(C$_6$F$_5$)$_4$] (about 50 μmol of [PhNMe$_2$H][B(C$_6$F$_5$)$_4$] and about 1.1 equiv of [NON]ZrMe$_2$) in chlorobenzene at 0° C.). The carefully weighed, limiting reagent was the "activator," [PhNMe$_2$H][B(C$_6$F$_5$)$_4$]. It is assumed that the amount of catalyst precursor formed is equal to the amount of activator when it is added to a 10% excess of [NON]ZrMe$_2$ in chlorobenzene. ([NON]ZrMe$_2$ itself is inactive.) The total volume of the reaction mixture was always 13.0 mL The reaction mixture was stirred for 1.5 hour and quenched by addition of HCl in diethyl ether (4 mL, 1.0 M). Most solvent was removed at 15 Torr (water aspirator) at 45° C.). The viscous oil was dried at 100 mTorr at 50–60° C. for 20 hours. Yields and molecular weight data are shown in Table 1. The molecular weights and polydispersities were measured by light scattering. The average value for dn/dc (0.049 mL/g) obtained (assuming total elution) from 18 runs (0.045 to 0.053 mL/g) was employed and M$_n$(found) calculated using that basis.

TABLE 1

| Equiv 1-hexene | μmol cat | M$_n$ (calcd) | M$_n$ (found) | M$_w$/M$_n$ |
| --- | --- | --- | --- | --- |
| 49 | 49 | 4144 | 5139 | 1.14 |
| 179 | 45 | 15026 | 15360 | 1.08 |
| 229 | 52 | 19210 | 19320 | 1.04 |
| 288 | 56 | 24262 | 24780 | 1.02 |
| 343 | 47 | 28901 | 24590 | 1.05 |
| 399 | 52 | 33592 | 35820 | 1.04 |

TABLE 1-continued

| Equiv 1-hexene | μmol cat | $M_n$ (calcd) | $M_n$ (found) | $M_w/M_n$ |
|---|---|---|---|---|
| 408 | 55 | 34349 | 28030 | 1.03 |
| 517 | 43 | 46430 | 39310 | 1.03 |

EXAMPLE 12

$H_2$[TMSNON] synthesis was performed as follows. A solution of BuLi in hexanes (33 mL, 1.6 M) was added to a solution of O(o-$C_6H_4NH_2)_2$ (5.04 g, 25.2 mmol) in THF (100 mL) at −35° C. The mixture was warmed up to room temperature and stirred for 5 h. TMSCl (7.3 mL, 58.0 mmol) was added at −35° C. The solution was warmed up to room temperature and stirred for 14 h. All volatile components were removed in vacuo and the residue extracted with pentane (60 mL) over a period of about 15 min. A white solid was filtered off (2.4 g) and washed with pentane (20 mL). All solvents were removed in vacuo to give an off-white solid; yield 8.29 g (95%): $^1$H NMR ($C_6D_6$) δ 6.88 (m, 6H), 6.59 (m, 2H), 4.22 (br s, 2H, NH), 0.095 (s, 18H, SiMe$_3$).

EXAMPLE 13

[TMSNON]ZrCl$_2$ synthesis was performed as follows. $H_2$[TMSNON] (1.29 g, 3.75 mmol) and Zr(NMe$_2$)$_4$ (1.00 g, 3.75 mmol) were dissolved in pentane (10 mL) at 25° C. After 18 hours all volatile components were removed in vacuo. The off-white residue was dissolved in diethyl ether (20 mL) and TMSCl (1.4 mL, 11.25 mmol) was added. After a few minutes a solid began to precipitate. After 90 min the volume of the mixture was reduced to about 10 mL and pentane (20 mL) was added. Copious amounts of pale yellow powder precipitated. All solvents were removed in vacuo ; yield 1.845 g (97%): $^1$H NMR ($C_6D_6$) δ 6.78 (m, 4H), 6.54 (m, 4H), 0.25 (s, 18H, SiMe$_3$).

EXAMPLE 14

[TMSNON]Zr$^{13}$Me$_2$ was prepared as follows. A solution of $^{13}$MeMgI in diethyl ether (1.4 mL, 0.9 M) was added to a suspension [TMSNON]ZrCl$_2$ (310 mg, 0.615 mmol) in diethyl ether at −35° C. The solution was warmed up to room temperature and stirred for about 15 min during which time a brown solid precipitates. 1,4-dioxane (108 mg, 1.23 mmol) was added and all volatile components removed in vacuo. The residue was extracted with pentane (10 mL) for about 5 min. The solid was filtered off and washed with more pentane (about 5 mL) affording a brown solid and a pale yellow filtrate. The filtrate was evaporated to dryness and the off-white residue recrystallized from a mixture of diethyl ether and pentane affording colorless crystalline product; yield 155 mg (54%): $^1$H NMR ($C_6D_6$) δ 6.85 (m, 6H), 6.54 (m, 2H), 0.81 (d, $J_{CH}$=114 Hz, 6H, Zr$^{13}$Me$_2$), 0.26 (s, 18H, SiMe$_3$); $^{13}$C NMR ($C_6D_6$) δ 47.16 ($^{13}$CH$_3$).

EXAMPLE 15

[TMSNON]Zr$^{13}$Me$_2$ was used as a polymerization initiator as follows. Inside the glove box a 100 mL flask was charged with Ph$_3$C[B($C_6F_5$)$_4$] (49 mg, 54 μmol) and chlorobenze (9 mL). [TMSNON]Zr$^{13}$Me$_2$ (25 mg, 54 μmol) was added as a solid under stirring at −35° C. The flask was capped with a rubber septum and quickly brought outside where it was cooled to 0° C. in an ice bath. After 5 min 1-hexene (1.5 mL) was injected with a gas tight syringe. After 30 min the mixture was quenched with HCl in diethyl ether (3 mL, 1 M). Removal of all volatile components afforded viscous material; yield 860 mg (80%). Gel permeation chromatography demonstrated a polydispersity of about 1.37.

EXAMPLE 16

(2,6-i—Pr$_2$—C$_6$H$_3$NHCH$_2$CH$_2$)$_2$O was prepared as follows. Solid (TsOCH$_2$CH$_2$)$_2$O (5 g, 12.0 mmol) was added to a chilled solution of 2,6-i—Pr$_2$—C$_6$H$_3$NHLi (4.53 g, 24.8 mmol) in THF (30 ml). After stirring at RT for 24 h all volatiles were removed in vacuo. The residue was extracted with pentane. Removal of all volatiles gave an orange oil (4.2 g, 82%) which could be used without further purification. The oil crystallized upon standing. $^1$H NMR ($C_6D_6$) δ 7.18–7.14 (br m, 6H, H$_{aromat}$), 3.60 (t, 2H, NH), 3.48 (sep, 4H, CHMe$_2$), 3.35 (t, 4H, OCH$_2$), 3.07 (q, 4H, CH$_2$N), 1.06 (d, 24 H, CHMe$_2$).

EXAMPLE 17

[(2,6-i—Pr$_2$—C$_6$H$_3$NCH$_2$CH$_2$)$_2$O]Zr(NMe$_2$)$_2$ was prepared as follows. A solution of Zr(NMe$_2$)$_4$ (2.5 g, 9.4 mmol) in pentane (4 ml) was added to a solution of (2,6-i—Pr$_2$—C$_6$H$_3$NHCH$_2$CH$_2$)$_2$O (4.0 g, 9.4 mmol) in pentane (14 ml). Almost instantaneous crystallization occurred. After standing overnight the crystals were collected and the mother liquor was cooled to −30° C. yielding a second crop of crystals. Total yield was 3.85 g (68%). $^1$H NMR ($C_6D_6$) δ 7.15–7.10 (br m, 6H, H$_{aromat}$), 3.71 (sep, 4H, CHMe$_2$), 3.56 (t, 4H, OCH$_2$), 3.33 (t, 4H, CH$_2$N), 2.56 (s, 12H, ZrNMe$_2$), 1.31 (d, 12 H, CHMe$_2$), 1.28 (d, 12 H, CHMe$_2$). $^{13}$C NMR ($C_6D_6$) δ 150.2 (Ph), 146.2 (o-Ph), 125.2 (p-Ph), 124.2 (m-Ph), 72.8 (OCH$_2$), 57.7 (CH$_2$N), 42.7 (ZrNMe$_2$) 29.0 (CHMe$_2$), 26.9 (CHMe$_2$), 25.4 (CHCMe$_2$).

EXAMPLE 18

[(2,6-i—Pr$_2$—C$_6$H$_3$NCH$_2$CH$_2$)$_2$O]ZrCl$_2$ was prepared as follows. Neat TMSCl (578 mg, 5.3 mmol) was added to a solution of [(2,6-i—Pr$_2$—C$_6$H$_3$NCH$_2$CH$_2$)$_2$O]Zr(NMe$_2$)$_2$ (400 mg, 0.664 mmol) in 10 ml diethyl ether at RT. After thorough mixing by vigorous shaking the reaction mixture was allowed to stand overnight at RT yielding colorless crystals (285 mg) in 73% yield. If the ethereal solution of [(2,6-i—Pr$_2$—C$_6$H$_3$NCH$_2$CH$_2$)$_2$O]Zr(NMe$_2$)$_2$ is too concentrated, [N$_2$O]Zr(NMe)Cl cocrystallizes with [(2,6-i—Pr$_2$—C$_6$H$_3$NCH$_2$CH$_2$)$_2$O]ZrCl$_2$. $^1$H NMR ($C_6D_6$) δ 7.17 (br, 4H, m-Ph), 7.15 (br, 6H, p-Ph), 3.73 (sep, 4H, CHMe$_2$), 3.66 (t, 4H, OCH$_2$), 3.35 (t, 4H, CH$_2$N), 1.51 (d, 12 H, CHMe$_2$), 1.26 (d, 12 H, CHMe$_2$). $^{13}$C NMR ($C_6D_6$) δ 146.4 (Ph), 145.1 (o-Ph), 127.6 (p-Ph), 125.1 (m-Ph), 73.6 (OCH$_2$), 59.3 (CH$_2$N), 29.0 (CHMe$_2$), 26.9 (CHMe$_2$), 25.4 (CHCMe$_2$).

EXAMPLE 19

[(2,6-i—Pr$_2$—C$_6$H$_3$NCH$_2$CH$_2$)$_2$O]Zr(CH$_2$CHMe$_2$)$_2$ was prepared as follows. A chilled solution of BrMgCH$_2$CHMe$_2$ (2.51 M in ether, 286 μl, 0.72 mmol) was added to a suspension of [(2,6-i—Pr$_2$—C$_6$H$_3$NCH$_2$CH$_2$)$_2$O]Zr (NMe$_2$)$_2$ (205 mg, 0.35 mmol) in diethyl ether (10 ml) at −30° C. A fine precipitate slowly replaced the suspension of crystals and after stirring for 1.5 h at RT dioxane (63 mg, 0.72 mmol) was added. After 20 min of additional stirring all volatiles were removed and the residue was extracted with pentane. Recrystallization from pentane yielded 158 mg (72%) of colorless crystals. $^1$H NMR ($C_6D_6$) δ 7.17–7.12 (br, 4H, H$_{Ar}$), 3.91 (sep, 4H, CHMe$_2$), 3.66 (br, 8H, OCH$_2$CH$_2$N), 1.92 (m, 2H, CH$_2$CHMe2), 1.45 (d, 12H, CHMe$_2$), 1.23 (d, 12H, CHMe$_2$), 0.85 (d, 12 H, CH$_2$CHMe$_2$), 0.70 (d, 4H, CH$_2$CHMe$_2$). $^{13}$C NMR (C$_6$D$_6$) δ 149.2 (C$_{ipso}$), 146.0 (o-Ar), 126.2 (p-Ar), 124.6 (m-Ar), 78.1 (CH$_2$CHMe$_2$), 74.5 (OCH$_2$), 58.3 (CH$_2$N), 29.7 (CH$_2$CHMe$_2$), 28.9 (CHMe$_2$), 28.4 (CH$_2$CHMe$_2$), 27.4 (CHMe$_2$), 24.6 (CHMe$_2$).

EXAMPLE 20

[(2,6-i—Pr$_2$—C$_6$H$_3$NCH$_2$CH$_2$)$_2$O]ZrMe$_2$ was prepared as follows. A chilled solution of BrMgMe (4.1 M in ether, 428 μl, 1.75 mol) was added to a suspension of [(2,6-i—Pr$_2$—C$_6$H$_3$NCH$_2$CH$_2$)$_2$O]ZrCl$_2$ (500 mg, 0.85 mmol) in diethyl ether (20 ml) at −30° C. A fine precipitate slowly replaced the suspension of crystals and after stirring for 2 h at RT dioxane (154 mg, 1.75 mmol) was added. After 20 min of additional stirring all volatiles were removed and the residue was extracted with pentane. Recrystallization from pentane yielded 280 mg (61%) of colorless crystals. $^1$H NMR (C$_6$D$_6$) δ 7.15 (br, 2H, p-Ar), 7.12 (br, 4H, m-Ar), 3.84 (sep, 4H, CHMe$_2$), 3.41 (br, 8H, OCH$_2$CH$_2$N), 1.38 (d, 12 H, CHMe$_2$), 1.23 (d, 12 H, CHMe$_2$),).30 (s, 6H, ZrMe). $^{13}$C NMR (C$_6$D$_6$) δ 147.1 (C$_{ipso}$), 146.5 (o-Ph), 126.5 (p-Ph), 124.7 (m-Ph), 73.6 (OCH$_2$), 58.6 (CH$_2$N), 43.6 (ZrMe), 28.9 (CHMe$_2$), 27.3 (CHMe$_2$), 24.9 (CHCMe$_2$).

EXAMPLE 21

[NON]Hf(NMe$_2$)$_2$ was synthesized as follows. [NON]H$_2$ (8.964 g, 0.027 mol) and Hf(NMe$_2$)$_4$ (9.800 g, 0.027 mol) were stirred in 40 mL toluene at 115° C. in a 100 mL sealed vessel for 30 hours. Solvents were then removed in vacuo and the resulting white microcrystalline solid was slurried in 20 mL pentane, collected on a frit, washed with several portions of pentane, and dried in vacuo; yield 10.141 g (62%). $^1$H NMR (C$_6$D$_6$) δ 7.06 (m, 2, Ar), 6.97 (m, 2, Ar), 6.90 (m, 2, Ar), 6.56 (m, 2, Ar), 3.01 (s, 12, NMe$_2$), 1.34 (s, 6, t-Bu);

EXAMPLE 22

[NON]HfCl$_2$ was prepared as follows. [NON]Hf(NMe$_2$)$_2$ (961 mg, 1.631 mmol) and TMSCl (1.063 g, 9.789 mmol) were stirred in 30 mL toluene at 100° C. for 5 hours during which a yellow color developed. Solvents were removed in vacuo and the resulting yellow solid was extracted with Et$_2$O/toluene (30 mL/10 mL), filtered, and solvents were removed to give the product as a canary yellow microcrystalline solid; yield 657 mg (70%): $^1$H NMR (C$_6$D$_6$) δ 6.80 (m, 6, Ar), 6.53 (m, 2, Ar), 1.31 (s, 6, t-Bu).

EXAMPLE 23

[NON]HfMe$_2$ was prepared as follows. A stirred pale yellow solution of [NON]HfCl$_2$ (152 mg, 0.266 mmol) in 7 mL Et$_2$O at −40° C. was treated with MeMgI (0.558 mmol, 2.8 M in Et$_2$O) whereupon MgClI precipitated immediately. The mixture was allowed to warm to 25° C. over 1 hour after which a few drops of 1,4-dioxane were added and the mixture was stirred for an additional 30 minutes. Solvents were removed in vacuo and the product was extracted from the white residue with 10 mL pentane, filtered through Celite, and the filtrate concentrated and stored at −40° C. overnight. Colorless prisms were separated from the mother liquor and dried in vacuo: yield 91 mg, (65%). $^1$H NMR (C$_6$D$_6$) δ 6.94–6.83 (m, 6, Ar), 6.54 (m, 2, Ar), 1.36 (s, 6, t-Bu), 0.65 (s, 6, Me) C$_{22}$H$_{20}$N$_2$D$_{12}$HfO: C, 49.76; H, 8.35 N, 5.27.

EXAMPLE 24

[NON]Hf(CH$_2$CH(CH$_3$)$_2$)$_2$ was prepared as follows. A stirred pale yellow solution of [NON]HfCl$_2$ (525 mg, 0.918 mmol) in 18 mL Et$_2$O at −40° C. was treated with (CH$_3$)$_2$CHCH$_2$MgCl (1.882 mmol, 2.5 M in Et$_2$O) whereupon MgCl$_2$ precipitated immediately. The mixture was allowed to warm to 25° C. over 2 hours after which a few drops of 1,4-dioxane were added and the mixture was stirred for an additional 30 minutes. Solvents were removed in vacuo and the product was extracted from the white residue with pentane, filtered through Celite, and the filtrate concentrated and stored at −40° C. Large colorless prisms were separated from the mother liquor and dried in vacuo: yield 324 mg, (57%). $^1$H NMR (C$_6$D$_6$) δ 7.02–6.85 (m, 6, Ar), 6.56 (m, 2, Ar), 2.43 (m, 2, CH$_2$CHC(CH$_3$)$_2$), 1.37 (s, 6, t-Bu), 1.16 (d, 12, CH$_2$CHC(CH$_3$)$_2$, 1.02 (d, 4, CH$_2$CHC (CH$_3$)$_2$, J$_{HH}$=6.9); $^{13}$C{$^1$H} NMR (C$_6$D$_6$) δ 148.29, 142.77, 126.64, 123.73, 120.18, 119.48, 92.22, 31.57, 31.35, 30.81 (m, CD$_3$), 29.84. Anal. Calcd for C$_{28}$H$_{32}$N$_2$D$_{12}$HfO: C, 54.66; H, 9.17 N, 4.55.

EXAMPLE 25

{[NON]HfMe}[B(C$_6$F$_5$)$_4$]was prepared as follows. Solid [NON]HfMe$_2$ (15 mg, 0.028 mmol) and Ph$_3$C[B(C$_6$F$_5$)$_4$] (26 mg, 0.028 mmol) were combined and then dissolved in 0.7 mL C$_6$D$_5$Br at 25° C. to give an orange solution. $^1$H NMR (C$_6$D$_5$Br) δ 7.68–6.75 (m, Ar), 2.03 (s, 3, Ph$_3$CMe), 1.19 (s, 6, t-Bu), 0.68 (b, 3, HfMe).

EXAMPLE 26

{[NON]HfMe(2,4-lutidine)}B(C$_6$F$_5$)$_4$ was prepared as follows. Solid [NON]HfMe$_2$ (15 mg, 0.028 mmol) and Ph$_3$C[B(C$_6$F$_5$)$_4$] (26 mg, 0.028 mmol) were combined and then dissolved in 0.7 mL C$_6$D$_5$Br in an NMR tube at 25° C. to give an orange solution. Then 2,4-lutidine (3 mg, 0.028 mmol) was syringed into the NMR tube whereupon the solution rapidly turned yellow. $^1$H NMR (C$_6$D$_5$Br) δ 8.39 (b, 1, 2,4-lut), 7.29–6.66 (m, Ar), 2.21 (b, 3, Me$_{ortho}$), 2.03 (s, Ph$_3$Me), 1.96 (s, 3, Me$_{para}$), 1.14 (s, 6, t-Bu), 0.63 (s, 3, HfMe).

EXAMPLE 27

{[NON]Hf(CH$_2$CHMe$_2$)(2,4-lutidine)}B(C$_6$F$_5$)$_4$ was prepared as follows. Solid [NON]Hf(CH$_2$CH(CH$_3$)$_2$)$_2$ (15 mg, 0.025 mmol) and Ph$_3$C[B(C$_6$F$_5$)$_4$] (23 mg, 0.025 mmol) were dissolved in 0.7 mL C$_6$D$_5$Br at 25° C. followed by treatment with 2,4-lutidine (3 mg, 0.025 mmol whereupon the orange solution turned yellow. $^1$H NMR (C$_6$D$_5$Br) δ 8.50 (b, 1, 2,4-lut), 7.18–6.82 (m, Ar), 5.44 (s, 1, Ph$_3$CH), 4.68 (s, CH$_2$C(CH$_3$)$_2$, 2.42 (b, 4, CH$_2$CH(CH$_3$)$_2$) and Me$_{ortho}$), 2.03 (s, 3, M$_{epara}$), 1.61 (s, CH$_2$C(CH$_3$)$_2$, 1.02 (b, 6, t-Bu), 0.94 (d, 2, CH$_2$CH(CH$_3$)$_2$), 0.73 (d, 6, CH$_2$CH(CH$_3$)$_2$).

EXAMPLE 28

Polymerization of 1-hexene by {[NON]HfMe}B(C$_6$F$_5$)$_4$. A solution of [NON]HfMe$_2$ (15 mg, 0.028 mmol) and 1-hexene (24 mg, 0.28 mmol) in 0.5 mL C$_6$D$_5$Br was combined with a solution of Ph$_3$C[B(C$_6$F$_5$)$_4$] (26 mg, 0.028 mmol) in 0.5 mL C$_6$D$_5$Br at −40°. The resulting orange solution was transferred to an NMR tube. $^1$H NMR after 10 minutes showed the presence of Ph$_3$CMe, no 1-hexene, and several featureless broad resonances in 0.8–1.70 ppm region. An additional 10 equivalents of 1-hexene (24 mg, 0.28 mmol) were syringed into the NMR tube. $^1$H NMR showed no remaining 1-hexene.

EXAMPLE 29

Hexene was polymerized as follows. A solution of [(2,6-i—Pr$_2$—C$_6$H$_3$NCH$_2$CH$_2$)$_2$O]Zr(CH$_2$CHMe$_2$)$_2$ (28 mg, 44 μmol) in PhCl (4 ml) was added to a suspension of [PhNMe$_2$H][B(C$_6$F$_5$)$_4$] (32 mg, 40 μmol) in PhCl (8 ml) at −30° and the upon warm up to room temperature for 15 min. The reaction mixture was cooled to 0° and hexene (1.0 ml, 8.0 mmol) was added in one shot. The reaction was quenched with HCl (1.0 M in ether, 4 ml) after 80 min. All volatiles were removed in vacuo (100 mTorr) at 120° C.

EXAMPLE 30

Hexene was polymerized as follows. Neat PhNMe$_2$ (5.1 μl, 40 μmol) and a solution of [(2,6-i—Pr$_2$—C$_6$H$_3$NCH$_2$CH$_2$)$_2$O]Zr(CH$_2$CHMe$_2$)$_2$ (28 mg, 44 μmol) in PhCl (4 ml) were subsequently added to a solution of Ph$_3$C[B(C$_6$F$_5$)$_4$] (37 mg, 40 μmol) in PhCl (8 ml) at −30° and the reaction mixture was allowed to warm up to 0°. Hexene (1.0 ml, 8.0 mmol) was added in one shot and after 80 min the reaction was quenched with HCl (1.0 M in ether, 4 ml). All volatiles were removed in vacuo (100 mTorr) at 120° C.

EXAMPLE 31

Hexene was polymerized as follows. A solution of [(2,6-i—Pr$_2$—C$_6$H$_3$NCH$_2$CH$_2$)$_2$O]ZrMe$_2$ (30 mg, 55 μmol) in PhCl (3 ml) was added to a suspension of [PhNMe$_2$H][B(C$_6$F$_5$)$_4$] (40 mg, 50 μmol) in PhCl (9 ml) at −30° and the reaction mixture stirred upon warm up to room temperature for 10 min. The reaction mixture was cooled to 0° and hexene (1.0 ml, 8.0 mmol) was added in one shot. The reaction was quenched with HCl (1.0 M in ether, 4 ml) after 80 min. All volatiles were removed in vacuo (100 mTorr) at 120° C.

EXAMPLE 32

Hexene was polymerized as follows. A solution of [(2,6-i—Pr$_2$—C$_6$H$_3$NCH$_2$CH$_2$)$_2$O]ZrMe$_2$ (24 mg, 44 μmol) in PhCl (2 ml) was added to a suspension of [Ph$_3$C][B(C$_6$F$_5$)$_4$] (37 mg, 40 μmol) in PhCl (8 ml) at −30°. The reaction mixture was mixed thoroughly by shaking and allowed to react at −30° for 5 min. Hexene (1.0 ml, 8.0 mmol) was added in one shot and the reaction mixture was kept at −30° until the reaction was quenched with HCl (1.0 M in ether, 4 ml) after 2 h. All volatiles were removed in vacuo (100 mTorr) at 120° C.

EXAMPLE 33

A block copolymer polyhexene and polynonene was prepared as follows. {[NON]ZrMe(PhNMe$_2$)}[B(C$_6$F$_5$)$_4$] (46 micromoles in 8.0 ml of chlorobenzene) was gene situ as described in example 11. 1-hexene (600 microliters) was added at 0° C. After 15 min an aliquot (1.0 ml) was taken and quenched. Addition of 1-nonene (700 microliters) to the catalyst precursor/polyhexene mixture and workup after 30 min yielded a polymer (756 mg) which showed a narrow, unimodal peak in the GPC (M$_w$/M$_n$=1.03). The molecular weight (Mn) was 23,600.

EXAMPLE 34

O[o-C$_6$H$_4$NHC(CD$_3$)$_2$CH$_3$]$_2$ (H$_2$[NON] was synthesized as follows. O(o-C$_6$H$_4$NH$_2$)$_2$ (18.8 g, 94 mmol) was dissolved in acetone-d$_6$ (120 g, 1.88 mol) and activated 4 molecular sieves (30 g) were added. After the condensation was complete (as judged by $^1$H NMR) the molecular sieves were filtered off and the unreacted ketone was removed in vacuo. The imine dissolved in diethylether (60 mL) was slowly added to a precooled solution (acetone/dry ice) of methyllithium in diethylether (270 mL, 0.88 M). The reaction mixture was allowed to warm up to room temperature. After 24 h the reaction mixture was quenched by pouring it slowly into a beaker filled with 500 mL of a mixture of ice and water. The product was extracted into hexane (3×100 mL) and the combined organic layers were filtered through a 35 cm long and 2.5 cm wide alumina column. The solvent was evaporated in vacuo to afford 16.7 g (55%) of the product as a viscous orange oil: $^1$H NMR (CDCl$_3$) δ 7.00 (m, 4H), 6.68 (m, 4H), 4.19 (br s, 2H, NH), 1.35 (s, 6H, CMe(CD$_3$)$_2$); $^{13}$C (CDC$_3$) δ 145.24, 138.34, 123.62, 117.76, 117.30, 115.96, 50.81, 29.81, 29.28 (m, C(CD$_3$)$_2$Me); MS (EI) m/e 324 (M$^+$). Anal. Calcd for C$_{20}$H$_{16}$D$_{12}$N$_2$O : C, 74.02; H, 8.70; N, 8.63. Found: C, 74.41; H, 8.94; N, 8.30.

Having thus described certain embodiments of the present invention, various alterations, modifications and improvements will be apparent to those of ordinary skill in the art. Such alterations, modifications and improvements are intended to be within the spirit and scope of the present invention. For example, in the aforementioned chemical species, some or all of the hydrogen atoms may be replaced with deuterium atoms. Accordingly, the foregoing description is by way of example only. The present invention is limited only as defined by the following claims and the equivalents thereto.

What is claimed is:

1. A composition of matter comprising a structure:

wherein X and Z are each group 15 atoms, R$_1$ and R$_2$ are each a hydrogen atom or group 14 atom-containing species and A is

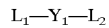

wherein Y$_1$ is a group 16 atom, and L$_1$ and L$_2$ include at least one group 14 atom bonded to Y$_1$.

2. The composition of matter according to claim 1, wherein the composition of matter has a structure:

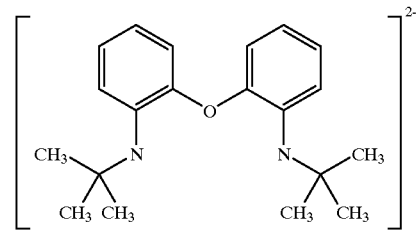

3. The composition of matter according to claim 1, wherein Y$_1$ is an atom selected from the group consisting of oxygen and sulfur.

4. The composition of matter according to claim 3, wherein X and Z are each nitrogen atoms.

5. The composition of matter according to claim 4, wherein L$_1$ and L$_2$ are bonded to X and Z respectively.

6. The composition of matter according to claim 3, wherein L$_1$ and L$_2$ are each C$_2$ units such that Y$_1$ is bonded to two carbon atoms.

7. The composition of matter according to claim 3, further comprising MR$_4$R$_5$ and having a structure:

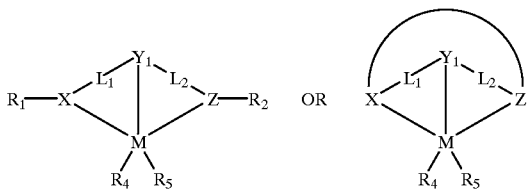

wherein M is a metal and $R_4$ and $R_5$ are each selected from the group consisting of halides and group 14 atom-containing species such that X and Z each form an anionic bond to M and $Y_1$ forms a bond to M and the composition of matter has no net charge.

8. The composition of matter according to claim 7, wherein M is selected from the group consisting of Ti, Zr, and Hf.

9. The composition of matter comprising a structure:

$$[R_1-X-A-Z-R_2]^{2-}$$

wherein X and Z are each group 15 atoms, $R_1$ and $R_2$ are each selected from the group consisting of hydrogen atoms, linear hydrocarbons, branched hydrocarbons and aromatic hydrocarbons and A is

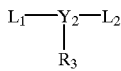

wherein $Y_2$ is a group 15 atom, $R_3$ is H or a group 14 atom-containing species and $L_1$ and $L_2$ include at least one group 14 atom bonded to $Y_2$.

10. The composition of matter according to claim 9, wherein X and Z are each nitrogen atoms.

11. The composition of matter according to claim 10, wherein $L_1$ and $L_2$ are bonded to X and Z respectively.

12. The composition of matter according to claim 9, wherein $L_1$ and $L_2$ are each $C_2$ units such that $Y_2$ is bonded to two carbon atoms.

13. The composition of matter according to claim 9, further comprising $MR_4R_5$ and having a structure:

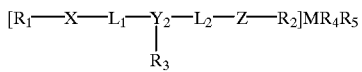

wherein M is a metal and $R_4$ and $R_5$ are each selected from the group consisting of halides and group 14 atom-containing species such that X and Z each form an anionic bond to M and $Y_2$ forms a bond to M and the composition of matter has no net charge.

14. The composition of matter according to claim 13, wherein M is selected from the group consisting of Ti, Zr, and Hf.

15. The composition of matter according to claim 10, wherein $Y_2$ is a nitrogen atom.

16. The composition of matter according to claim 15, wherein $L_1$ and $L_2$ are bonded to X and Z, respectively.

17. The composition of matter according to claim 16, wherein $L_1$ and $L_2$ are each $C_2$ units such that $Y_2$ is bonded to two carbon atoms.

18. The composition of matter according to claim 17, wherein $R_1$ and $R_2$ are each aromatic hydrocarbons and $R_3$ is H.

19. The composition of matter according to claim 17, wherein $R_1$ and $R_2$ are each linear hydrocarbons and $R_3$ is H.

20. The composition of matter according to claim 17, wherein $R_1$ and $R_2$ are each branched hydrocarbons and $R_3$ is H.

21. The composition of matter according to claim 17, wherein $R_1$ and $R_2$ are each aromatic hydrocarbons and $R_3$ is a group 14 atom-containing species.

22. The composition of matter according to claim 17, wherein $R_1$ and $R_2$ are each linear hydrocarbons and $R_3$ is a group 14 atom-containing species.

23. The composition of matter according to claim 17, wherein $R_1$ and $R_2$ are each branched hydrocarbons and $R_3$ is a group 14 atom-containing species.

24. The composition of matter according to claim 17, wherein $R_1$, $R_2$ and $R_3$ are each H.

25. The composition of matter according to any one of claims 15 to 24, further comprising $MR_4R_5$ and having a structure:

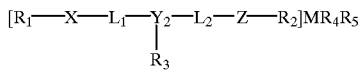

wherein M is a metal and $R_4$ and $R_5$ are each selected from the group consisting of halides and group 14 atom-containing species such that X and Z each form an anionic bond to M and $Y_2$ forms a dative bond to M and the composition of matter has no net charge.

26. The composition of matter according to claim 25, wherein M is selected from the group consisting of Ti, Zr, and Hf.

* * * * *